United States Patent
Schendel et al.

(10) Patent No.: US 9,238,063 B2
(45) Date of Patent: *Jan. 19, 2016

(54) SEMI-ALLOGENIC ANTI-TUMOUR VACCINE WITH HLA HAPLO-IDENTICAL ANTIGEN-PRESENTING CELLS

(75) Inventors: Dolores Schendel, Munich (DE); Rudolf Wank, Munich (DE)

(73) Assignee: Helmholtz Zentrum München Deutsches Forschungszentrum für Gesundlheit und Umwelt (GmbH), Neuhberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/027,827

(22) Filed: Feb. 15, 2011

(65) Prior Publication Data

US 2011/0182945 A1 Jul. 28, 2011

Related U.S. Application Data

(63) Continuation of application No. 10/665,111, filed on Sep. 16, 2003, now Pat. No. 8,206,701, which is a continuation of application No. 10/663,421, filed on Sep. 15, 2003, now abandoned, which is a continuation of application No. PCT/EP02/02595, filed on Mar. 8, 2002, said application No. 10/665,111 is a continuation of application No. PCT/EP02/02595.

(30) Foreign Application Priority Data

Mar. 16, 2001 (DE) .................................. 101 12 851

(51) Int. Cl.
| | | |
|---|---|---|
| A61K 35/15 | (2015.01) | |
| A61K 35/28 | (2015.01) | |
| A61K 48/00 | (2006.01) | |
| A61K 39/00 | (2006.01) | |
| C12N 5/10 | (2006.01) | |
| C12N 5/078 | (2010.01) | |

(52) U.S. Cl.
CPC ............ *A61K 39/0011* (2013.01); *A61K 48/00* (2013.01); *A61K 2039/5154* (2013.01); *A61K 2039/5156* (2013.01)

(58) Field of Classification Search
None
See application file for complete search history.

(56) References Cited

U.S. PATENT DOCUMENTS

| | | | |
|---|---|---|---|
| 4,415,553 A | 11/1983 | Zhabilov et al. | |
| 4,568,542 A | 2/1986 | Kronenberg | |
| 4,703,004 A | 10/1987 | Hopp et al. | |
| 4,789,658 A | 12/1988 | Yoshimoto et al. | |
| 4,851,341 A | 7/1989 | Hopp et al. | |
| 4,877,611 A | 10/1989 | Cantrell | |
| 5,156,841 A | 10/1992 | Rapp | |
| 5,290,551 A | 3/1994 | Berd | |
| 5,582,831 A | 12/1996 | Shinitzky | |
| 5,906,936 A | 5/1999 | Eshhar et al. | |
| 6,063,375 A | 5/2000 | Newton et al. | |
| 6,077,519 A | 6/2000 | Storkus et al. | |
| 6,143,292 A | 11/2000 | Slavin | |
| 6,458,585 B1 | 10/2002 | Vachula et al. | |
| 6,805,861 B2 | 10/2004 | Stauss | |
| 7,659,084 B2 | 2/2010 | Frentsch et al. | |
| 8,206,701 B2 | 6/2012 | Schendel et al. | |
| 8,486,694 B2 | 7/2013 | Schendel et al. | |
| 2002/0123479 A1 | 9/2002 | Song et al. | |
| 2002/0168351 A1 | 11/2002 | Ohno | |
| 2004/0260061 A1 | 12/2004 | Kaltoft | |
| 2005/0175596 A1 | 8/2005 | Schendel | |
| 2010/0189728 A1 | 7/2010 | Schendel et al. | |
| 2011/0020308 A1 | 1/2011 | Schendel | |
| 2011/0280889 A1 | 11/2011 | Schendel et al. | |
| 2011/0280894 A1 | 11/2011 | Krackhardt et al. | |

FOREIGN PATENT DOCUMENTS

| | | |
|---|---|---|
| EP | 1 275 400 | 11/2004 |
| EP | 1 870 418 | 12/2007 |
| EP | 1 878 744 | 1/2008 |
| JP | 2001/500731 | 1/2001 |
| WO | WO96/04314 | 2/1996 |
| WO | WO97/04802 | 2/1997 |
| WO | WO97/26328 | 7/1997 |
| WO | WO97/32603 | 9/1997 |
| WO | WO97/41210 | 11/1997 |
| WO | WO98/11202 | 3/1998 |
| WO | WO98/33527 | 8/1998 |
| WO | WO98/58956 | 12/1998 |
| WO | WO99/03976 | 1/1999 |
| WO | WO 00/76537 | 12/2000 |
| WO | WO01/36680 | 5/2001 |
| WO | WO02/36790 | 5/2002 |
| WO | WO02/074338 | 9/2002 |

(Continued)

OTHER PUBLICATIONS

Butterfield et al (Journal of Immunology, 1998, vol. 161, pp. 5607-5613).*

(Continued)

*Primary Examiner* — Karen Canella
(74) *Attorney, Agent, or Firm* — Clark & Elbing LLP; Karen L. Elbing

(57) ABSTRACT

The present invention relates to semi-allogeneic antigen-presenting cells into which proteins and/or peptides or RNA or DNA or cDNA, respectively, encoding said proteins and/or peptides which are overexpressed in tumor cells or which are derived from autologous tumor cells or different tumor cells or different tumor cell lines have been introduced. Furthermore the invention relates to methods for the generation of these semi-allogeneic antigen-presenting cells as well as to the use thereof in the treatment of tumor diseases.

9 Claims, 2 Drawing Sheets

(56) References Cited

FOREIGN PATENT DOCUMENTS

Figure 1:
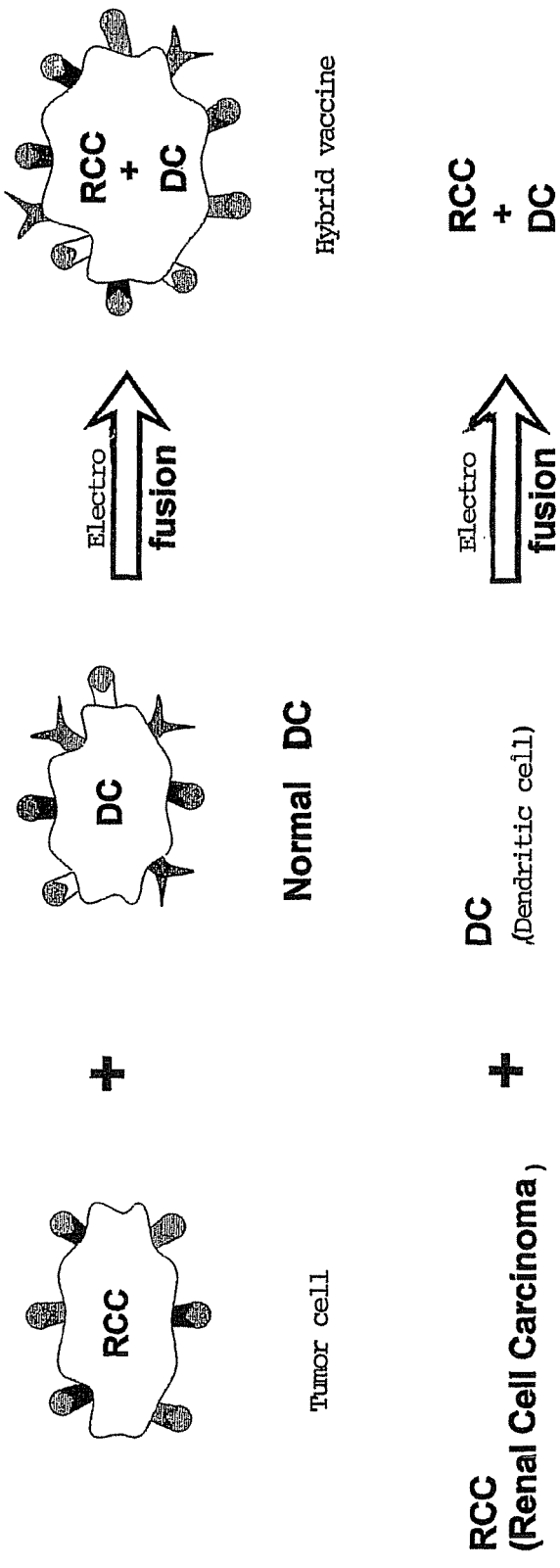

| WO | WO 03/045427 | * | 6/2003 |
|---|---|---|---|
| WO | WO2004/027428 | | 4/2004 |
| WO | WO2006/031221 | | 3/2006 |
| WO | WO2006/065495 | | 6/2006 |
| WO | WO2007/065957 | | 6/2007 |
| WO | WO2007/131092 | | 11/2007 |
| WO | WO2008/039818 | | 4/2008 |
| WO | WO2008/071701 | | 6/2008 |
| WO | WO2010/012829 | | 2/2010 |
| WO | WO2010/058023 | | 5/2010 |

OTHER PUBLICATIONS

Boczkowski et al (Journal of Experimental Medicine, 1996, vol. 184, pp. 465-472).*
Trevor et al (Cancer Immunology, Immunotherapy, 2001, vol. 50, pp. 397-407).*
Abstract of Wheeler (Salud p'ublica de M'exico, (Jul.-Aug. 1997) 39 (4) 283-7).
Altman, J. D. et al. (1996). "Phenotypic Analysis of Antigen-specific T Lymphocytes," Science 274:94-96.
Bachman et al (Journal of Immunology, 2005, vol. 175, pp. 4677-4685).
Boczkowski, D. et al. (2000). "Induction of Tumor Immunity and Cytotoxic T Lymphocyte Responses Using Dendritic Cells Transfected with Messenger RNA Amplified from Tumor Cells," Cancer Res 60: 1028-1 034.
Childs, R. et al., "Regression of Metastatic Renal-Cell Carcinoma After Nonmyeloablative Allogeneic Peripheral-Blood Stem Cell Transplantation," N. Engl. J. Med., vol. 343, No. 11, pp. 750-758 (2000).
Da et al., "Autologous bone marrow mixed with HLA-haploidentical allogeneic marrow transplantation for treatment of patients with malignant blood diseases," Bone Marrow Transplantation, vol. 19, pp. 107-112 (1997).
Dannull, J. et al. (2000). "Current Status of Dendritic Cell-Based Tumor Vaccination," Onkologie 23:544-551.
Efferson et al (Anticancer research, 2005, vol. 25, pp. 715-724).
Genbank Accession No. 97478808.
Gong, J. et al. (2000). "Fusions of Human Ovarian Carcinoma Cells with Autologous or Allogeneic Dendritic Cells Induce Antitumor Immunity," J. Immunology 165: 1705-1711.
Heiser, A. et al. (2000). "Human Dendritic Cells Transfected with RNA Encoding.Prostate-Specific Antigen Stimulate Prostate Specific CTL Responses in Vitro," J. Immunol. 164:5508-5014.
Jantzer, P. et al. (1998). "Human Renal Cell Carcinoma Antigen-Specific Cytotoxic T Lymphocytes: Antigen-Driven Selection and Long-Tenn Persistence in Vivo," Cancer Res. 58:3078-3086.
Kolb, H.-J et al. (1995). "Graft-Versus-Leukemia Effect of Donor Lymphocyte Transfusions in Marrow Grafted Patients," Blood 86(5):2041-2050.
Kufe, D. (2000). "Smallpox. Polio and Now a Cancer Vaccine?" Nature Med 6(3):252-253.
Kugler, A. et al. (2000). "Regression of Human Metastatic Renal Cell Carcinoma After Vaccination With Tumor Cell-Dendritic Cell Hybrids," Nature Med. 6:332-336.
Kugler, A. et al. (Sep. 2003). Retraction: "Regression of Human Metastatic Renal Cell Carcinoma After Vaccination with Tumor Cell-Dendritic Cell Hybrids," Nature Medicine 9(9):1221. (on server).
Nair et al., "Induction of Carcinoembryonic Antigen (CEA)-Specific Cytotoxic T—Lymphocyte Responses in Vitro Using Autologous Dendritic Cells Loaded with CEA Peptide or CEA RNA in Patients with Metastatic Malignancies Expressing CEA," Int. J. Cancer, vol. 82.
Nair, S. K., "Induction of Primary Carcinoembryonic Antigen (CEA)-Specific Cytotoxic T Lymphocytes In Vitro Using Human Dendritic Cells Transfected with RNA," Nat. Biotechnol., vol. 16, pp. 364-369 (1998).

Official Action corresponding to Japanese Patent Application No. JP 2002-573045 dated Nov. 18, 2008.
Official Action corresponding to U.S. Appl. No. 10/665,111 dated Jan. 21, 2010.
Official Action corresponding to U.S. Appl. No. 10/665,111 dated Jun. 10, 2009.
Official Action corresponding to U.S. Appl. No. 10/665,111 dated Nov. 20, 2008.
Official Action corresponding to U.S. Appl. No. 10/665,111 dated Sep. 4, 2007.
Official Action corresponding to U.S. Appl. No. 10/665,111 dated Dec. 27, 2006.
Official Action corresponding to U.S. Appl. No. 10/665,111 dated Jun. 28, 2006.
Official Action corresponding to U.S. Appl. No. 10/665,111 dated Jun. 11, 2008.
Philip et al., "Transgeneexpression in dendritic cells to induce antigen-specific cytotoxic T cells in healthy donors," Cancer Gene Therapy, vol. 5, pp. 236-246 (1988).
Schendel et al. "Expression of B7.I (CD80) in a Renal Cell Carcinoma Line Allows Expansion of Tumor-Associated Cytotoxic T Lymphocytes in the Presence of an Alloresponse," Gene Therapy, vol. 7, pp. 2007-2014. (2000).
Schendel, et al. "Tumor-Specific Recognition of Human Renal Cell Carcinomas by Tumor-Infiltrating Lymphocytes. 1. HLA-A2 Restricted Lysis of Autologous and Aliogeneic Tumor Lines," J. Immunol., vol. 151, pp. 4209-4220. (1993).
Speck et al., "Treatment of severe aplastic anaemia with antilymphocyte globulin or bone-marrow transplantation," British Medical Journal, vol. 282, pp. 860-863 (Mar. 14, 1981).
Stedman's Medical dictionary, 2000, definition for "vaccine".
Su et al. "Antigen Presenting Cells Transfected with LMP2a RNA Induce CD4+ LMP2a-Specific Cytotoxic T Lymphocytes which Kill Via a Fas-Independent Mechanism," Leukemia and Lymphoma, vol. 43(S), pp. 1651-1662. (2002).
Su et al. "The Generation of LMP2a-Specific Cytotoxic T Lymphocytes for the Treatment of Patients with Epstein-Barr Virus—Positive Hodgkin Disease," Eur. J. Immunol., vol. 31, pp. 947-958 (2001).
Visseren et al., "CTL Specific for the Tyrosinase Autoantigen•Can Be Induced from Healthy Spender Blood to Lyse Melanoma Cells," J. Immunol., vol. 154, pp. 3991-3998. (1995).
Notice of Allowance corresponding to U.S. Appl. No. 10/665,111 dated Feb. 21, 2012.
Official Action corresponding to U.S. Appl. No. 10/665,111 dated Aug. 16, 2011.
Alajez et al., "Therapeutic potential of a tumor-specific, MHC-unrestricted T-cell receptor expressed on effector cells of the innate and the adaptive immune system through bone marrow transduction and immune reconstitution," Blood. vol. 105, No. 12 pp. 4583-4589 (2005).
Bernhard et al., "Adoptive transfer of autologous, HER2-specific, cytotoxic T lymphocytes for the treatment of HER2-overexpressing breast cancer," Cancer Immunology, Immunotherapy. vol. 57, No. 2 pp. 271-280 (2008).
Bishop et al., "Allogeneic Lymphocytes Induce Tumor Regression of Advanced Metastatic Breast Cancer," Journal of Clinical Oncology. vol. 22, No. 19 pp. 3886-3892 (2004).
Blaise et al., "Reduced-intensity preparative regimen and allogeneic stem cell transplantation for advanced solid tumors," Blood. vol. 103, No. 2 pp. 435-441 (2004).
Clay et al., "Efficient Transfer of a Tumor Antigen-Reactive TCR to Human Peripheral Blood Lymphocytes Confers Anti-Tumor Reactivity," The Journal of Immunology. vol. 163, No. 1 pp. 507-513 (1999).
Cobleigh et al., "Multinational Study of the Efficacy and Safety of Humanized Anti-HER2 Monoclonal Antibody in Women Who Have HER2-Overexpressing Metastatic Breast Cancer That Has Progressed After Chemotherapy for Metastatic Disease," Journal of Clinical Oncology. vol. 17, No. 9 pp. 2639-2648 (1999).
Cohen et al., "Enhanced Antitumor Activity of Murine-Human Hybrid T-Cell Receptor (TCR) in Human Lymphocytes Is Associated with Improved Pairing and TCR/CD3 Stability," Cancer Research. vol. 66, No. 17 pp. 8878-8886 (2006).

(56) References Cited

OTHER PUBLICATIONS

Dawicki, W., and Watts, T.H., "Expression and function of 4-1BB during CD4 versus CD8 T cell repsonses in vivo," European Journal of Immunology, vol. 34 No. 3 pp. 743-751 (2004).

de Witte et al., "Targeting self-antigens through allogeneic TCR gene transfer," Blood. vol. 108, No. 3 pp. 870-877 (2006).

Disis et al., "Generation of T-Cell Immunity to the HER-2/neu Protein After Active Immunization With HER-2/neu Peptide-Based Vaccines," Journal of Clinical Oncology. vol. 20, No. 11 pp. 2624-2632 (2002).

Dudley et al., "Cancer regression and autoimmunity in patients after clonal repopulation with antitumor lymphocytes," Science. vol. 298 pp. 850-854 (2002).

Dudley et al., "Adoptive Cell Transfer Therapy Following Non-Myeloablative but Lymphodepleting Chemotherapy for the Treatment of Patients With Refractory Metastatic Melanoma," Journal of Clinical Oncology. vol. 23, No. 10 pp. 2346-2357 (2005):

Dupont et al., "Artificial Antigen-Presenting Cells Transduced with Telomerase Efficiently Expand Epitope-Specific, Human Leukocyte Antigen-Restricted Cytotoxic T Cells," Cancer Research. vol. 65, No. 12 pp. 5417-5427 (2005).

Engels et al., "Redirecting Human T Lymphocytes Toward Renal Cell Carcinoma Specificity by Retroviral Transfer of T Cell Receptor Genes," Human Gene Therapy. vol. 16, No. 7 pp. 799-810 (2005).

European Search Report corresponding to European Patent Application No. 10 179 257.0-1222 dated Oct. 26, 2010.

Gao et al., "Allo-Major Histocompatibility Complex-Restricted Cytotoxid T Lymphocytes Engraft in Bone Marrow Transplant Recipients Without Causing Graft-Versus-Host Disease," Blood. vol. 94, No. 9 pp. 2999-3006 (1999).

Gao et al., "Selective elimination of leukemic CD34+ progenitor cells by cytotoxic T lymphocytes specific for WT1," Blood. vol. 95, No. 7 pp. 2198-2203 (2000).

Geiger et al., "A generic RNA-pulsed dendritic cell vaccine strategy for renal cell carcinoma," Journal of Translational Medicine. vol. 3 (15 pages) (2005).

Gilboa, E., and Viewig, J., "Cancer immunotherapy with mRNA-transfected dendritic cells," Immunological Reviews. vol. 199 pp. 251-263 (2004).

Goyarts et al., "Point mutations in the β chain CDR3 can alter the T cell receptor recognition pattern on an MHC class I/peptide complex over a broad interface area," Molecular Immunology vol. 35 No. 10 pp. 593-607 (1998).

Greten et al., "Peptide-(2-microglobulin-MHC fusion molecules bind antigen-specific T cells and can be used for multivalent MHC-lg complexes," Journal of Immunological Methods. vol. 271, Nos. 1-2 pp. 125-135 (2002).

Heemskerk et al., "Redirection of antileukemic reactivity of peripheral T lymphocytes using gene transfer of minor histocomatibility antigen HA-2-specific T-cell receptor complexes expressing a conserved alpha joining region," Blood. vol. 102 pp. 3530-3540 (2003).

Ho et al., "In vitro methods for generating CD8+ T-cell clones for immunotherapy from the naïve repertoire," Journal of Immunological Methods. vol. 310 pp. 40-52 (2006).

Intent to Grant corresponding to European Patent Application No. 09 760 145.4—2115 dated May 22, 2012.

Kazatchkine, "Nomenclature for T-cell receptor (TCR) gene segments of the immune system," WHO-IUIS Nomenclature Sub-Committee on TCR Designation. Immunogenetics. vol. 42, No. 6 pp. 451-453 (1995).

Kieback et al., "A safeguard eliminates T cell receptor gene-modified autoreactive T cells after adoptive transfer," PNAS. vol. 105, No. 2 pp. 623-628 (2008).

Knabel et al., "Reversible MHC multimer staining for funtional isolation of T-cell populations and effective adoptive transfer," Nature Medicine. vol. 8, No. 6 pp. 631-637 (2002).

Knutson et al., "Immunization of Cancer Patients with a HER-2/neu, HLA-A2 Peptide, p. 369-377, Results in Short-lived Peptide-specific Immunity," Clinical Cancer Research. vol. 8, No. 5 pp. 1014-1018 (2002).

Krackhardt et al., "Identification of tumor-associated antigens in chronic lymphocytic leukemia by SEREX," Blood. vol. 100, No. 6 pp. 2123-2131 (2002).

Kuntson et al., "Clonal Diversity of the T-Cell Population Responding to a Dominant HLA-A2 Epitope of HER/2/neu After Active Immunization in an Ovarian Cancer Patient," Human Immunology vol. 63 pp. 547-557 (2002).

Lattrich et al., "Detection of an elevated HER2 experssion in MCF-7 breast cancer cells overexpressing estrogen receptor β1," Oncology Reports vol. 19 pp. 811-817 (2008).

Leisegang et al., "Enhanced functionality of T cell receptor-redirected T cells is defined by the transgene cassette," Journal of Molecular Medicine. vol. 86, No. 5 pp. 573-583 (2008).

Levings, M.K., and Roncarolo, M.G., "Phenotypic and Functional Differences Between Human CD4+CD25+ and Type 1 Regulatory T Cells," Current Topics in Microbiology and Immunology. vol. 293 pp. 303-326 (2005).

Manning et al., "Alanine Scanning Mutagenesis of an αβ T cell Receptor: Mapping the Energy of Antigen Recognition," Immunity.

Marzio et al. "CD69 and Regulation of the Immune Function," Immunopharmacology and Immunotoxicology. vol. 21, No. 3 pp. 565-582 (1999).

Mittendorf et al., "Evaluation of the HER2/neu-Derived Peptide GP2 for Use in a Peptide-Based Breast Cancer Vaccine Trial," Cancer. vol. 106, No. 11 pp. 2309-2317 (2006).

Mittendorf et al., "Investigating the Combination of Trastuzumab and HER2/neu Peptide Vaccines for the Treatment of Breast Cancer," Annals of Surgical Oncology. vol. 13, No. 8 pp. 1085-1098 (2006).

Morgan et al., "Cancer Regression in Patients After of Genetically Engineered Lymphocytes," Science. vol. 314, No. 5796 pp. 126-129 (2006).

Moris et al., "Cutting Edge: Characterization of Allorestricted and Peptide-Selective Alloreactive T Cells Using HLA-Tetramer Selection," The Journal of Immunology. vol. 166, No. 8 pp. 4818-4821 (2001).

Morris et al., "Prospects for immunotherapy of malignant disease," Clinical and Experimental Immunology. vol. 131, No. 1 pp. 1-7 (2003).

Murphy et al., "Gene modification strategies to induce tumor immunity," Immunity vol. 22 pp. 403-414 (2005).

Moris et al., "Generation of minor histocompatibilty antigen HA-1-specific cytotoxic T cells restricted by nonself HLA molecules: a potential strategy to treat relapsed leukemia after HLA-mismatched stem cell transplantation," Blood vol. 100, No. 2 pp. 547-552 (2002).

Napolitani et al., "Selected Toll-like receptor agonist combinations synergistically trigger a T helper type 1-polarizina program in dendritic cells," Nature Immunology. vol. 6, No. 8 pp. 769-776 (2005).

Neudorfer et al., "Reversible HLA multimers (Streptamers) for the isolation of human cytotoxic T lymphocytes functionally active against tumor- and virus derived antigens," Journal of Immumological Methods. vol. 320, Nos. 1-2 pp. 119-131 (2007).

Notice of Allowance corresponding to U.S. Appl. No. 11/990,054 dated Apr. 16, 2013.

Notification Concerning Transmittal of International Preliminary Report on Patentability (Chapter I of the Patent Cooperation Treaty) corresponding to International Patent Application No. PCT/EP2007/063704 dated Jun. 25, 2009.

Notification Concerning Transmittal of International Preliminary Report on Patentability (Chapter I of the Patent Cooperation Treaty) corresponding to International Patent Application No. PCT/EP2009/059953 dated Feb. 10, 2011.

Notification Concerning Transmittal of International Preliminary Report on Patentability (Chapter I of the Patent Cooperation Treaty) corresponding to International Patent Application No. PCT/EP2009/065705 dated Jun. 3, 2011.

Notification of Transmittal of International Search Report and the Written Opinion of the International Searching Authority, or the Declaration corresponding to International Patent Application No. PCT/EP2006/007752 dated Jan. 23, 2007.

Notification of Transmittal of the International Preliminary Report on Patentability corresponding to International Patent Application No. PCT/EP2006/007752 dated Sep. 27, 2007.

(56) References Cited

OTHER PUBLICATIONS

Notification of Transmittal of the International Search Report and the Written Opinion of the International Searching Authority, or the Declaration corresponding to International Patent Application No. PCT/EP2007/063704 dated Mar. 17, 2008.
Notification of Transmittal of the International Search Report and the Written Opinion of the International Searching Authority, or the Declaration corresponding to International Patent Application No. PCT/EP2009/059953 dated Nov. 20, 2009.
Notification of Transmittal of the International Search Report and the Written Opinion on the International Searching Authority, or the Declaration corresponding to International Patent Application No. PCT/EP2009/065705 dated Mar. 4, 2010.
Nückel et al., "HLA-G expression is associated with an unfavorable outcome and immunodeficiency in chronic lymphocytic leukemia." Blood. vol. 105, No. 4 pp. 1694-1698 (2005).
Oelke et al., "Technological Advances in Adoptive Immunotherapy," Drugs of Today. vol. 41, No. 1 pp. 13-21 (2005).
Official Action corresponding to Chinese Patent Application 200980154272 dated Mar. 19, 2013. [Translation].
Official Action corresponding to U.S. Appl. No. 11/990,054 dated Feb. 26, 2013.
Official Action corresponding to U.S. Appl. No. 11/990,054 dated Jul. 11, 2011.
Official Action corresponding to U.S. Appl. No. 11/990,054 dated May 3, 2012.
Official Action corresponding to U.S. Appl. No. 12/517,995 dated May 3, 2012.
Official Action corresponding to U.S. Appl. No. 13/056,827 dated Mar. 29, 2013.
Official Action corresponding to U.S. Appl. No. 13/056,827 dated Nov. 6, 2012.
Official Action corresponding to U.S. Appl. No. 13/130,665 dated Feb. 21, 2013.
Official Action corresponding to U.S. Appl. No. 13/130,665 dated May 16, 2013.
Papanicolaou et al., "Rapid expansion of cytomegalovirus—specific cytotoxic T lymphocytes by artificial antigen-presenting cells expressing a single HLA allele," Blood. vol. 102, No. 7 pp. 2498-2505 (2003).
Peoples et al., "Breast and ovarian cancer-specific cytotoxic T lymphocytes recognize the same HER2/neu-derived peptide," PNAS, vol. 92 pp. 432-436 (1995).
Peoples et al., "Clinical Trial Results of a HER2/neu (E75) Vaccine to Prevent Recurrence in High-Risk Breast Cancer Patients," Journal of Clinical Oncology. vol. 23, No. 30 pp. 7536-7545 (2005).
Regn et al., "Ex vivo generation of cytotoxic T lymphocytes specific for one or two distinct viruses for the prophylaxis of patients receiving an allogenic bone marrow transplant," Bone Marrow Transplantation. vol. 27 pp. 53-64 (2001).
Rongcun et al., "Identification of New HER2/neu-Derived Peptide Epitopes That Can Elicit Specific CTL Against Autologous and Allogeneic Carcinomas and Melanomas," The Journal of Immunology. vol. 163, No. 2 pp. 1037-1044 (1999).
Rossig et al., "Genetic modification of T lymphocytes for adoptive immunotherapy," Molecular Therapy vol. 10 No. 1 pp. 5-18 (2004).
Roth et al., "Analysis of T Cell Receptor Transcripts Using the Polymerase Chain Reaction," BioTechniques. vol. 7, No. 7 pp. 746-754 (1989).
Saskia et al., "In vitro priming of tumor-specific cytotoxic T lymphocytes using allogeneic dendritic cells derived from the human MUTZ-3 cell line," Cancer Immunol Immunother vol. 55 pp. 1480-1490 (2006).
Savage et al. "A Kinetic Basis for T cell Receptor Repertoire Selection during an Immune Response," Immunity. vol. 10, No. 4 pp. 485-492 (1999).

Schaft et al., "Generation of an Optimized Polyvalent Monocyte-Derived Dendritic Cell Vaccine by Transfecting Defined RNAs after Rather Than before Maturation," The Journal of Immunology. vol. 174, No. 5 pp. 3087-3097 (2005).
Scholten et al., "Codon modification of T cell receptors allows enhanced functional expression in transgenic human T cells," Clinical Immunology. vol. 119 pp. 135-145 (2006).
Schumacher, "T-cell-receptor gene therapy," Nat Rev Immunol. vol. 2 pp. 512-519 (2002).
Schuster et al., "Allorestricted T cells with specificity for the FMNL1-derived peptide PP2 have potent antitumor activity against hematologic and other malignancies," Blood. vol. 110, No. 8 pp. 2931-2939 (2007).
Slamon et al., "Human Breast Cancer: Correlation of Relapse and Survival with Amplification of the HER-2/neu Oncogene," Science. vol. 235, No. 4785 pp. 177-182 (1987).
Slamon et al., "Use of Chemotherapy Plus a Monoclonal Antibody Against HER2 for Metastatic Breast Cancer That Overespresses HER2," The New England Journal of Medicine. vol. 344, No. 11 pp. 783-792 (2001).
Sommermeyer et al., "Designer T cells by T cell receptor replacement," European Journal of Immunology. vol. 36 pp. 3052-3059 (2006).
Stanislawski et al., "Circumventing tolerance to a human MDM2-derived tumor antigen by TCR gene transfer," Nature Immunology. vol. 2, No. 10 pp. 962-970 (2001).
Toes et al., "CD40-CD40Ligand interactions and their role in cytotoxic T lymphocyte priming and anti-tumor immunity," Seminars in Immunology. vol. 10, No. 6, pp. 443-448 (1998).
Vanclée et al., "Graft-versus-tumor effects on murine mammary carcinoma in a model of nonmyeloablative haploidentical stem cell transportation," Bone Marrow Transplantation. vol. 37 pp. 1043-1049 (2006).
Visseren et al., "Affinity, Specificity and T-Cell-Receptor Diversity of Melanoma-Specific CTL Generated In Vitro Against A Single Tyrosine Epitope," International Journal of Cancer. vol. 72, No. 6 pp. 1122-1128 (1997).
Wölfel et al., "Analysis of Antigens Recognized on Human Melanoma Cells By A2-Restricted Cytolytic T Lymphocytes (CTL)," International Journal of Cancer. vol. 55 pp. 237-244 (1993).
Xue et al., "Elimination of human leukemia cells in NOD/SCID mice by WT1-TCR gene-transduced human T cells," Blood. vol. 106, No. 9 pp. 3062-3067 (2005).
Xue et al., "Exploiting T cell Receptor genes for cancer immunotherapy," Clin. Exp. Immunol. vol. 139 pp. 167-172 (2005).
Yee et al., "Isolation of High Avidity Melanoma-Reactive CTL from Heterogeneous Populations Using Peptide-MHC Tetramers," The Journal of Immunology. vol. 162, No. 4 pp. 2227-2234 (1999).
Zaks, T.Z., and Rosenberg, S.A., "Immunization with a Peptide Epitope (p369-377) from HER-2/neu Leads to Peptide-specific Cytotoxic T Lymphocytes That Fail to Recognize HER-2/neu+ Tumors," Cancer Research. vol. 58, No. 21 pp. 4902-4908 (1998).
Decision to Grant corresponding to European Patent Application No. 06776623.8-1222 / 1910521 dated Sep. 16, 2010.
Official Action corresponding to European Patent Application No. 09 781 360.4-1404 dated Jun. 19, 2013.
Official Action corresponding to European Patent Application No. 10 179 257.0-1222 dated Feb. 7, 2012.
Official Action corresponding to Singapore Patent Application No. SG 2011033909-9 dated Apr. 18, 2013.
Rudolph et al., "How TCRs Bind MHCs, Peptides, and Coreceptors," Annu. Rev. Immunol. vol. 24 pp. 419-466 (2006).
Ex Parte Quale Action corresponding to U.S. Appl. No. 11/990,054 dated Feb. 26, 2013.
Notice of Allowance corresponding to U.S. Appl. No. 13/130,665 dated Dec. 6, 2013.
Official Action corresponding to U.S. Appl. No. 13/056,827 dated Nov. 22, 2013.

\* cited by examiner

SEMI-ALLOGENIC ANTI-TUMOUR VACCINE WITH HLA HAPLO-IDENTICAL ANTIGEN-PRESENTING CELLS

CROSS-REFERENCE TO RELATED APPLICATIONS

This application is a continuation of U.S. patent application Ser. No. 10/665,111, filed Sep. 16, 2003 now U.S. Pat. No. 8,206,701, which is a continuation of U.S. patent application Ser. No. 10/663,421, filed Sep. 15, 2003 now abandoned, which is a continuation of International Patent Application No. PCT/EP02/02595, filed Mar. 8, 2002, which claims priority under 35 U.S.C. §119 to German Patent Application No. 101 12851.7, filed Mar. 16, 2001, the disclosures of which are all herein incorporated by reference in their entirety.

This application is also a continuation of U.S. patent application Ser. No. 10/665,111, filed Sep. 16, 2003, which is a continuation of International Patent Application No. PCT/EP02/02595, filed Mar. 8, 2002, which claims priority under 35 U.S.C. §119 to German Patent Application No. 101 12851.7, filed Mar. 16, 2001, the disclosures of which are all herein incorporated by reference in their entirety.

The present invention relates to semi-allogeneic antigen-presenting cells into which proteins and/or peptides or RNA or DNA or cDNA encoding said proteins and/or peptides which are overexpressed in tumor cells or which are derived from tumor cells have been introduced. Furthermore the invention relates to methods for the generation of these semi-allogeneic antigen-presenting cells as well as to the use thereof in the treatment of tumor diseases.

Three recent developments suggest that cell-mediated immune reactions may result in a significant reduction in tumor load and in a similarly significant prolongation of the survival time of the patients in the case of tumor diseases such as for example a metastatic renal cell carcinoma (mRCC). Clinical data have already demonstrated a success in the case of mRCC but it is also contemplated to transfer the same principles to other tumors. In the following, three developments will be described which form the basis of the approach according to the invention.

I. Allogeneic Bone Marrow Transplantation for the Treatment of Metastatic Renal Cell Carcinoma Renal cell carcinoma patients subjected to allogeneic bone marrow transplantation may achieve a complete or partial remission in 53% of the cases (1). The life expectancy may be significantly increased from several months to several years. While important tumor loads may be eliminated, 53% of the patients develop a graft-versus-host disease (GVDH) accompanied by a GVDH-associated mortality of 5%.

The mechanism of tumor regression presumably is comparable to that associated with the elimination of hematological malignomas following allogeneic bone marrow transplantation (BMT) (2). Activated T lymphocytes recognize ligands consisting of peptides derived from a protein expressed in tumor cells and MHC, molecules (both of the class I and the class II type). The MHC proteins are classified into three groups two of which, namely the MHC class I and class II proteins, are of particular importance in the present invention. In humans the MHC class I proteins are referred to as HLA-A, -B, -C. They are expressed on the surface of almost any body cell and represent strong transplantation antigens showing a high degree of polymorphism. The MHC class II proteins in humans are HLA-DP, -DQ, -DR and are for example expressed on dendritic cells and stimulated macrophages and also represent highly polymorphic transplantation antigens.

Ligand recognition activates effector functions (for example cytokine secretion and cytotoxicity) in various T cells, whereby a destruction of tumor cells is effected. The parallel activation of T cells which recognize ligands composed of MHC and non-tumor associated peptides (i.e. alloreactions) may contribute to an optimal immune reaction by the secretion of inflammatory cytokines which themselves promote the anti-tumor reaction. However, the reactions of these cells also play a role in GVHD.

II. Hybrid Vaccines Using Autologous Tumor Cells and Allogeneic Dendritic Cells (DC)

Kugler et al. (3, 4) have shown that mRCC patients may be "vaccinated" by hybrid vaccines consisting of fused allogeneic dendritic cells and autologous tumor cells of non-related individuals. Following the "vaccination" the patients show a marked reduction in tumor load. Fewer patients achieve a complete remission as compared to approach I, and an increased life expectancy has not been observed so far. In contrast to the treatment in approach I, however, the hybrid vaccine approach shows no or only a slight toxicity. After the termination of the vaccination some tumor patients suffered from a relapse presumably due to a lack of sustenance of long-term T cell reactions. It may be possible to overcome this problem by a continuous vaccination, however, the vaccination is limited by the availability of tumor cells serving as fusion partners for the allogeneic dendritic cells. Thus it is impossible to continue the treatment if the tumor cells are declining.

III. RNA Obtained from Tumor Cells for the Generation of Vaccines on the Basis of Autologous DCs Gilboa and coworkers (5-8) have developed a strategy for priming autologous DCs with autologous RNA prepared from tumor cells which can be incorporated by DCs, translated into a protein and processed into peptides for presentation with autologous MHC class I and class II molecules. To provide an unlimited source of material for DC pulsing, RNA from tumor cells is transcribed back into cDNA which then serves as a template for in vitro transcription of further RNA. A PCR amplification enables the generation of material in unlimited amounts. The expression of RNA obtained from tumor cells in autologous DCs enables the expression on the surface of DCs of MHC-peptide ligands corresponding to those expressed on the tumor cell surface. The co-stimulatory molecules of the DC and the cytokines that it produces enable an optimal stimulation of T cell reactions. These vaccines show only a slight toxicity, however, no remission comparable to those of I and II has been published to date. This may be attributable to a lack in alloresponsive cells which are not activated in an autologous system.

In summary it may be concluded that the conventional therapy approaches suffer from substantial disadvantages preventing a long-term therapeutic success or entraining severe undesirable effects.

Thus, as already described above, approach I suffers from the risk of GVHD development occurring in 53% of cases and partially associated with a lethal outcome.

The approach described under II (Kugler et al.) has the disadvantage that viable tumor cells of the patient are required to provide the MHC-peptide ligands and the approach thus is strongly limited in its application period.

Although the therapy according to Gilboa and coworkers shows only a slight toxicity, no remarkable tumor remission has been published so far.

Therefore it is an object of the present invention to provide antigen-presenting cells avoiding the disadvantages cited above which thus are useful in the therapy of tumor diseases.

This object has been achieved by the features described in the independent claims. Preferred embodiments are mentioned in the dependent claims.

By using semi-allogeneic antigen-presenting cells into which have been introduced the proteins and/or peptides or RNA or DNA or cDNA, respectively, encoding said proteins and/or peptides which are overexpressed in tumor cells or are derived from autologous tumor cells or from several different tumor cell lines an immune reaction may be achieved which is advantageous for the treatment of tumor diseases.

Different from the approach of Kugler et al. the method according to the invention for the generation of these semi-allogeneic antigen-presenting cells has the advantage that electrofusion is not necessary. The function of the antigen-presenting cells thus is not disturbed by electrofusion. An electrofusion can be avoided because transfection, for example with RNA, utilizes the natural capability of antigen-presenting cells to incorporate such molecules.

The strategy according to the invention, i.e. the use of a semi-allogeneic vaccine provides a higher presentation efficiency of the ligands consisting of MHC and tumor-associated peptide. Only about 10% of hybrid cells are generated by the approach of Kugler et al. while according to the invention a clearly higher percentage of antigen-presenting cells expressing the peptide ligand can be generated.

In this respect the approach used according to a preferred embodiment for an (unlimited) generation of tumor-associated RNA is particularly advantageous by which e.g. RNA derived from autologous tumor cells is reverse transcribed, the cDNA is amplified by means of PCR and subsequently the cDNA is transcribed into RNA.

This approach according to the invention has the advantage that already minor amounts of tumor cells can provide sufficient RNA to form an unlimited source of cDNA for in vitro RNA transcription. By pulsing on the basis of RNA it is thus possible to avoid the disadvantages accompanied by a limited amount of tumor cells. Long-term possibilities to perform vaccinations improve the reaction rates and the long-term prevalence thereof as compared to for example the approach according to Kugler et al.

MHC molecules of semi-allogeneic antigen-presenting cells which do not correspond to the MHC molecules of the patients provide a stimulus for alloreactions. Thus, by using semi-allogeneic antigen-presenting cells an enhanced immune reaction is provoked in comparison to the use of autologous cells. Nevertheless the toxicity of the vaccine according to the invention is much lower than that of the approaches described so far.

The use of semi-allogeneic dendritic cells according to the invention thus provides the necessary MHC matching according to the approach of Gilboa et al. while avoiding the disadvantage accompanying the use of autologous dendritic cells that the function of autologous dendritic cells is weak and often associated with an advanced disease of cancer patients.

According to the invention, antigen-presenting cells are prepared from individuals which are semi-allogeneic with respect to the patient. This is the case if the MHC molecules of antigen-presenting cells of a related donor, e.g. father, mother, brothers and sisters, or offspring, are 50% identical to the MHC molecules of the patient. This may be schematically demonstrated as follows: if the patient HLA has the alleles a+c, close relatives being potential donors must have the following allelic variants:

Parents: HLA ab or cd
Brothers and sisters: HLA ad or bc
Offspring: HLA ae, af, ce, cf
(mother=HLA ef)

Insofar, the semi-allogeneic antigen-presenting cells mentioned above are HLA-haploidentical with respect to those of the patient and therefore may also be referred to as HLA-haploidentical antigen-presenting cells.

HLA-haploidentical antigen-presenting cells have class (HLA-A, -B, and -C) molecules in common with the patient which are encoded by the HLA-A, -B, and -C alleles of one chromosome. They also have class II molecules (HLA-DR, -DQ, and -DP) in common with the patient encoded by the corresponding alleles of the same chromosome.

Following the isolation of the semi-allogeneic antigen-presenting cells proteins and/or peptides or RNA or DNA or cDNA or cRNA, respectively, encoding said proteins and/or peptides derived from autologous tumor cells are introduced into these cells. In another embodiment proteins and/or peptides or RNA, DNA, cDNA, or cRNA encoding said proteins and/or peptides which are overexpressed in tumor cells are introduced. These are tumor-defined antigens, i.e. antigens specific for tumor cells and having a higher expression or markedly higher expression, respectively, in tumor cells as compared to normal cells. Preferably, such tumor-defined antigens are selected from oncogenes, for example HER2/neu, proteins providing a growth advantage to the tumor and/or ensuring its survival, e.g. PSMA, cell cycle regulatory proteins, transcription factors, e.g. WT-1, mucins, preferably MUC-1, proteins involved in the regulation of cell division, preferably telomerase. It should be understood that the proteins, peptides, RNA, DNA, cDNA, and cRNA mentioned herein can also be prepared and used in a recombinant manner.

As a result the antigen-presenting cells present a ligand consisting of MHC and tumor-associated peptide which is recognized by T cells and thus induces an immune reaction directed against the autologous tumor.

According to a preferred embodiment the use of antigen-presenting cells of two different semi-allogeneic donors (i.e. for example mother and father) is provided so that the MHCs presented by the semi-allogeneic DCs comprise all potential MHC class I and class II molecules of the patient. The second chromosome of each donor additionally encodes allogeneic MHC molecules which may serve to induce alloreactions.

In order to provide MHC class I and class II peptide ligands corresponding to those of the patient's tumor cells the already known strategy according to Gilboa and coworkers is used to provide an unlimited source of tumor-derived RNA for the pulsing of antigen-presenting cells. An equivalent possibility is to pulse the semi-allogeneic antigen-presenting cells with other sources of antigen, for example peptides and proteins (9).

According to one embodiment of the invention the proteins and/or peptides or RNA or DNA, cDNA, or cRNA, respectively, encoding said proteins and/or peptides overexpressed in tumor cells or derived from autologous tumor cells are derived from tumor cells, preferably autologous tumor cells or are overexpressed in said tumor cells, respectively, wherein the tumor cells comprise: cells of mesenchymal tumors, e.g. cells of sarcomas, carcinomas, preferably ovarian, mammary and renal cell carcinomas, tumor cells of the hematopoietic system, preferably cells of leukemias and lymphomas, cells of epithelial tumors, cells of ectodermal tumors, e.g. melanomas, and cells of embryonic tumors from undifferentiated tissue, preferably blastomas and teratomas. A particular example for the renal cell carcinomas which is examined in more detail herein is the metastatic renal cell carcinoma. The semi-allogeneic antigen-presenting cells according to the invention may then be used in the treatment of the tumors.

As already mentioned above the RNA from autologous tumor cells intended for the incorporation into the antigen-presenting cells may be reverse transcribed into cDNA for infinite amplification, the cDNA may be amplified by means of PCR, and the cDNA may be then transcribed into RNA.

The administration of the antigen-presenting cells according to the invention is carried out by the intravenous, subcutaneous or intramuscular routes wherein subcutaneous injection is preferred.

For the use in the present invention all types of antigen-presenting cells may be used. These particularly include monocytes/macrophages and dendritic cells of which the latter are preferred.

Another aspect of the present invention is that instead of components of autologous tumor cells there is used a pool of components of several different tumor cell lines which is introduced into the semi-allogeneic antigen-presenting cells. These may then be used as vaccines in tumor treatment. To generate such a "generic" vaccine it is advantageous to prepare for example a pool of cDNA as described above of 3-5 different RCCs which may then be used for all patients. Namely, it can be assumed that most of the tumor-specific T cells primed against such pool-pulsed antigen-presenting cells can recognize autologous tumor cells due to the fact that they have peptide-MHC ligands in common. This means that it is sufficient to generate a single product (i.e. a generic cDNA and the corresponding cRNA transcribed in vitro) under GMP conditions (GMP=Good Manufacturing Practice). Afterwards it will be required to prepare only the semi-allogeneic dendritic cells for each patient who is to be treated by the vaccine therapy according to the invention under GMP conditions.

Eventually, the present invention comprises a pharmaceutical composition containing semi-allogeneic antigen-presenting cells described above wherein said composition preferably is in the form of a vaccine.

Figure 2:
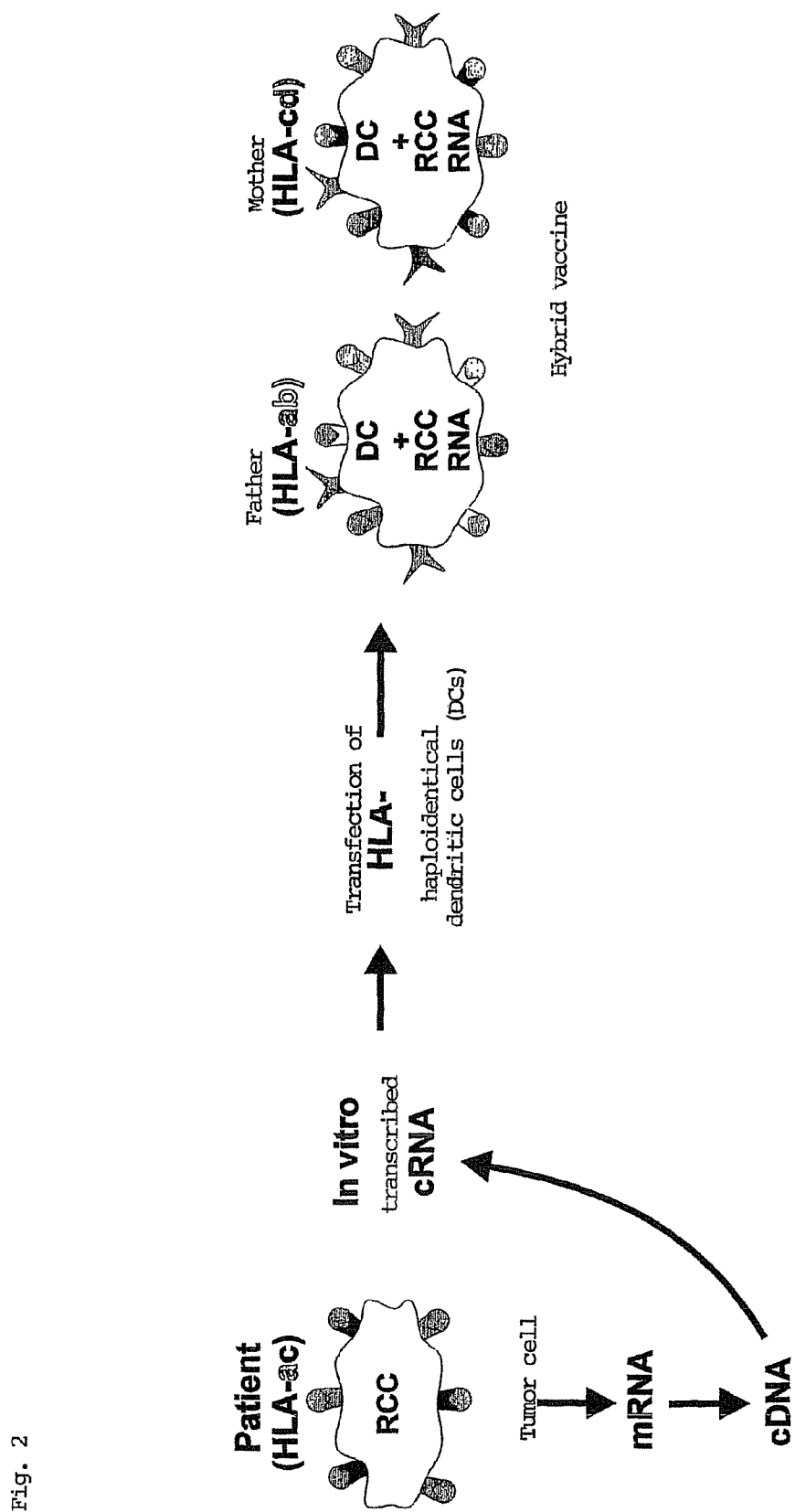

The Figures show:

FIG. 1 the principle of the generation of an allogeneic tumor vaccine according to Kugler et al. wherein an autologous tumor cell and an allogeneic dendritic Cell of non-related individuals are fused;

FIG. 2 the approach according to the invention wherein a semi-allogeneic vaccine is generated by using HLA-haploidentical antigen-presenting cells.

The haplospecific vaccines present the following features:
ligands consisting of MHC and TAA (tumor associated antigen) peptide for half of the patient alleles;
all alleles may be matched by means of two haploidentical DC preparations;
HLA mismatched MHC-peptide ligands for stimulation of alloreactions and T helper cells;
costimulatory molecules and cytokines derived from Ds for an optimal promotion of the immune reactions (represented as "Y" in the Figure).

In the following the basic principles of the invention as well as test models serving for the illustration thereof will be described in more detail using dendritic cells as an example.

Two model systems will be used to establish the principles of this approach. The first uses a well characterized set of reagents from a melanoma model and the second uses a set of reagents from a renal Cell carcinoma model. The melanoma model has the advantage that the epitope (MHC-peptide ligand) seen by the T cell receptor (TCR) of the test clone (Tyr-F8) has been defined; this allows the efficiency of antigen presentation by antigen-presenting cells such as dendritic cells to be analyzed in a more quantitative fashion. The epitope for one renal cell carcinoma specific T cell clone (TIL-26) has not yet been identified but these cytotoxic T lymphocytes (CTLs) utilize highly characteristic TCRs which can be identified and quantified in vitro with the method of real time RT-PCR based on the molecular sequence of the TCR CDR3 region. This enables the assessment of the functional priming capacity of the dendritic cells by identifying T cells through these characteristic TCR sequences. Combined, these two models can be used to demonstrate the specificity and the efficiency of this system for presenting tumor-associated peptides at the surface of the DCs and for activating specific T cell responses in vitro. These are essential experiments to establish proof of principle prior to development of a phase I/II clinical trial.

Melanoma System

The reagents for this Model system were obtained from Prof. Peter Schrier of the University of Leiden. An HLA-A*O201-restricted CTL clone (Tyr F8) was isolated from a patient with advanced melanoma. An autologous melanoma tumor cell line from the patient was also established. The specific ligand, i.e. the peptide derived from a tumor-associated protein is known; it is derived from tyrosinase, an enzyme that is expressed at normal levels in healthy melanocytes but which is overexpressed in the melanoma. The MHC presenting molecule was identified to be encoded by the HLA-A*O201 allele. The cDNA for tyrosinase is available; the exact nine amino acid peptide derived from the tyrosinase protein that is presented in the peptide binding groove of the HLA-A2 molecule is known and the Tyr F8 T cell clone is available (10).

The general outline of the experiment is first to prepare RNA from the melanoma line and then to prepare cDNA by reverse transcription. This cDNA is then amplified and used as a template to prepare in vitro transcribed RNA (cRNA). The cRNA is used to pulse HLA-A2-positive dendritic cells (11, 12). These dendritic cells will take up the cRNA, and then translate it into proteins, one protein of which should be the tyrosinase enzyme. The tyrosine protein is processed intracellularly in the dendritic cells into peptide fragments and the specific nine amino acid epitope is loaded onto newly synthesized HLA-A2 molecules in the endoplasmic reticulum of the dendritic cells. These MHC-peptide complexes are then transported to the plasma membrane of the dendritic cell where they can be recognized by T cells. Tyr F8 cells recognizing the appropriate MHC-peptide complex on the DC surface respond by secreting interferon-gamma and activating the cytolytic mechanism, allowing them to kill the dendritic cell. This activation can be assessed by ELISA detection of interferon-gamma secretion by the Tyr F8 clone or by using a standard chromium release assay, labeling the dendritic cells as target cells and measuring their lysis in the presence of Tyr F8 cells. The activation of the Tyr F8 cells is very specific so that MHC molecules carrying peptides derived from proteins other then tyrosinase can not activate the Tyr F8 cells and a certain threshold of these specific MHC-tyrosinase peptide complexes must be presented by the DC in order to optimally stimulate the activity of the Tyr F8 cells.

To determine whether the original cRNA can provide the necessary starting material to allow the dendritic cell to fulfill all these steps, cRNA-pulsed dendritic cells are used as stimulating cells to activate the Tyr F6 cells. Because the melanoma tumor cells yield a variety of different RNAs, transcripts for tyrosinase represent only one component of a much larger pool. The capacity of this mixed cRNA pool to provide the tyrosinase epitope can be compared to cRNA made from the isolated tyrosinase cDNA (i.e. only one RNA species). A relative assessment of the level of HLA-A2-tyrosinase-peptide complexes can be determined by pulsing dendritic cells with varying amounts of test cRNA and comparing their stimulatory capacity with dendritic cells that have been pulsed with varying known amounts of synthetic peptide, representing the nine amino acid epitope of tyrosinase. The threshold level at which the Tyr F8 cells can no longer detect the correct MHC-peptide complex can be determined by assessing the amount of interferon-gamma released by Tyr F8 cells using a specific ELISA assay.

Renal Cell Carcinoma System

These reagents have been established by the inventors. We have isolated a CTL line specific for renal cell carcinoma from a renal cell carcinoma patient and T cell clones have been established from this T cell line (TIL-26). Autologous tumor cells were also obtained from this patient (RCC-26). The MHC restriction molecule presenting a tumor-associated peptide displayed by RCC-26 cells has been identified as the HLA-A*0201-encoded molecule. When the TIL-26 cells were exposed to the autologous RCC-26 tumor cells they were activated to secrete interferon-gamma and they were able to lyse the autologous RCC-26 tumor cells (13).

The general outline of the experiment is similar to that described for the melanoma system. In the first step, RNA will be made from RCC-26 cells and cDNA will be prepared by reverse transcription. This serves as the template to generate cRNA by in vitro transcription. The cRNA is used to pulse the dendritic cells and these dendritic cells are assessed for their capacity to activate the TIL-26 cells to secrete interferon-gamma. The dendritic cells are also assessed as target cells following pulsing with cRNA derived from RCC-26 cells in cytotoxicity assays using activated TIL-26 cells. The efficiency of stimulation of the dendritic cells can be compared with that of the RCC-26 cells, in assays measuring interferon-gamma secretion by the TIL-26 cells and as target cells in cytotoxicity assays.

These two sets of experiments clearly demonstrate that the procedure for generating MHC-peptide complexes using cRNA-pulsed allogeneic (HLA-A*0201) dendritic cells is functional.

Induction of T Cell Responses by cRNA-Pulsed Allogeneic Dendritic Cells:

To assess the capacity of the cRNA-pulsed dendritic cells to prime allogeneic T cells in vitro two experiments are performed in vitro. First, it was shown that naive T cells from donor DS (DS=anonymous donor) can be primed in vitro with RCC-26 tumor cells to recognize an epitope that is apparently the same as that seen by TIL-26 (14). Like TIL-26 cells, the T cells from donor DS express TCRα chains that are highly homologous to those expressed by TIL-26 cells (15). The TCR sequence of these T cells can be quantified by isolating RNA from a test sample and using TCR-specific primers to analyze the amount of transcripts in the samples using the method of real time RT-PCR (14). First, allogeneic HLA-A*0201-positive dendritic cells pulsed with cRNA (RCC-26-derived) are used as stimulating cells in mixed lymphocyte cultures using peripheral blood lymphocytes (PBL) of donor DS as responding cells. The emergence of the marker (Va2O) T cells recognizing the same epitope seen by TIL-26 cells is monitored by looking for increases in transcripts with characteristic Va2O sequences. A quantitative assessment can be made using real time RT-PCR comparing the frequency of such transcripts in the unstimulated PBLs and following stimulation with the cRNA-pulsed dendritic cells in vitro after various rounds of restimulation. Autologous dendritic cells derived from donor DS pulsed with cRNA (RCC-26-derived) are used as target cells and compared directly to RCC-26 tumor cells using, as cytotoxic effector cells, the PBLs primed with cRNA-pulsed dendritic cells versus PBLs primed with intact RCC-26 tumor cells.

As a second test system, T cells from an HLA-A*O201 donor are stimulated with cRNA-pulsed (melanoma-derived) dendritic cells which are derived from a donor expressing HLA-A*O201 in mixed lymphocyte-dendritic cell cultured. The development of T cells recognizing the tyrosine-specific ligand is assessed by standard flow cytometry using HLA-A2-tyrosinase peptide-specific tetramers (7).

Pulsing of Dendritic Cells with Mixed cRNA Samples:

It is currently assumed that immune responses generated against multiple epitopes will provide the best possibility to eliminate tumor cells and to protect against tumor relapse. This is based on observations that CTLs primed in vivo against individual MHC-peptide ligands have led to the generation of CTLs specific for the MHC-peptide ligand and, in some instances, to tumor regression. But tumor variants may emerge that no longer express the MHC molecules or no longer express the protein from which the specific peptide is derived. If CTLs of many different MHC-peptide ligand specificities are generated then it may be less feasible for tumor variants to emerge because individual tumor cells would need to express different mutations in all MHC molecules and proteins providing peptides, in order to escape detection by CTLs with many different specificities.

Therefore, it is optimal to pool cRNA from several tumor cell lines in order to provide many different tumor-associated peptides for immune attack. Similarly, it is also better to have several different MHC molecules shared by the responding T cells and the stimulating dendritic cells. This is achieved according to the strategy described herein by using HLA-haploidentical dendritic cells derived from family members of the donor of the T cells, as described below. However, it must be ensured that by pooling cRNA from different tumors the required density of MHC-peptide ligands characteristic for specific epitopes of one tumor cell line is still retained. This can be addressed experimentally by combining cRNA from the melanoma line with cRNA from the RCC-26 line. This pooled cRNA is then used to pulse allogeneic (HLA-A*O201-positive) dendritic cells and to assess whether these dendritic cells are still capable of activating both the melanoma-specific CTL clone, namely Tyr F8, and the RCC-specific clone, namely TIL-26. If this experiment shows that pooled cRNA (mixed at a ratio of 1:1 from the two tumor cRNAs) functions to activate both T cell clones, then variations in the ratio of the two cRNAs can be used to determine the degree to which a single cRNA sample can be diluted and still functions in DC processing and presentation, respectively. On the basis of pooled cRNA from several different tumor lines (for example, three RCC lines) a vaccine will then be generated and additional cRNAs will be added to this pool which have been derived from known genes expressed in various renal cell carcinomas that are also potential target molecules for specific CTLs. These could include HER2/neu, MUC1, PSMA, WT-1, telomerase and several other candidates (9). The influence of the addition of these individual cRNA species can be assessed by adding them to the cRNA of RCC-26 and testing the pulsed dendritic cells for their ability to activate TIL-26 cells.

Comparison of Autologous Versus HLA-Haploidentical Dendritic Cells as Antigen-Presenting Cells:

The experiments described above were designed to establish the use of cRNA-pulsed allogeneic dendritic cells obtained from unrelated donors that share only HLA- A*0201-encoded molecules with the responding T cells. The next step is then to demonstrate that HLA-haploidentical dendritic cells can prime T cells against tumor-associated epitopes transferred into the dendritic cells by cRNA. This strategy is chosen because HLA-haploidentical DCs share three class I alleles (HLA-A, B, and C) and three class II alleles (HLA-DR, -DQ and -DP) with the T cells. The different class 1 molecules can each bind a unique set of peptides and prime different CD8+ CTLs, and the three class II-encoded molecules also each bind different sets of peptides that are distinct from those of the class I molecules. These class II-peptide ligands activate another type of T lymphocyte, the CD4 cells, which can provide cytokines that support the optimal development of an immune response or function directly as effector cells (11).

The experiments analyzing the role of HLA-haploidentical dendritic cells will be done by comparing autologous dendritic cells prepared from a normal control donor (donor #1) and HLA-haploidentical dendritic cells prepared from a selected HLA-typed family member (donor #2) (i.e. a parent or sibling is selected to have one HLA haplotype in common with donor 1 and the second HLA-haplotype is mismatched; see FIG. 2). DCs prepared from both donors will be pulsed with the cRNA of RCC-26 or the melanoma line. The resulting DCs will first be tested for their capacity to stimulate interferon-gamma secretion from Tyr F8 and TIL-26 cells, as described above. In the next step, PBLs from donor #1 will be stimulated in vitro with cRNA-pulsed autologous dendritic cells or the HLA-haploidentical dendritic cells of donor 2. Following two or more rounds of restimulation, the presence of T cells recognizing epitopes presented by different MHC molecules (both class I and class II) will be assessed by measuring their interferon-gamma secretion following stimulation with cRNA-pulsed autologous dendritic cells in the absence and presence of specific monoclonal antibodies. The MHC class I-specific monoclonal antibodies (W6/32) will block interactions of CD8+ CTLs with the dendritic cells. Decreased interferon-gamma secretion in the presence of monoclonal antibodies specific for HLA-A, -B or -C molecules will demonstrate the degree to which CTLs seeing their peptides in association with different class I molecules are present. The presence of class II-restricted CD4+ cells can be elucidated by the same approach but instead using class II-specific monoclonal antibodies, reacting with HLA-DR, -DQ and -DP molecules (17).

The generation of cRNA according to the invention will be illustrated by the following flow chart:

Flow Chart for Preparation of cRNA

1) Grow tumor cell lines in vitro (for example melanoma line 9304.A 12 and the renal cell carcinoma line, RCC-26)
2) Extract RNA from the tumor cell lines (for example using Quigen "RNAEasy" Kit #75412)
3) Make first strand cDNA synthesis (for example using Clontech "Smart PCR" cDNA synthesis kit #K1 052)
4) Perform cDNA amplification (for example using Clontech "Smart PCR" cDNA synthesis kit #K1052)
5) Perform in vitro transcription of cDNA (for example using Ambion "mMessage-mMachine" kit #1344)
6) Purify cRNA (for example using Quigen "RNAEasy" kit #75142)
7) Test integrity of cRNA (for example using Perkin Elmer "One Step RT/PCR" kit #P/N4308206)

REFERENCES

1. Childs, R. W. Chernoff, A., Contentin, N., Bahceci, E., Schrump, D., Leitman, S., Read, E. J., Tisdale, J., Dunbar, C., Linehan, W. M., Young, N. S. and Barrett, A. J. 2000. Regression of metastiatic renal-cell carcinoma after non-myeloablative allogeneic peripheral-blood stem-cell transplantation. N. Engl. J. Med. 14:750-758.
2. Kolb, H.-J., Schattenberg., A., Goldman, J. M., Hertenstein, B., Jacobsen, N., Arcese, W., Ljungman, P., Ferrant, A., Verdonck, L., Niederwieder, D., van Rhee, F., Mittermuller, J., de Witte, T., Holler, E. and Ansara, H. for the European Group for Blood and Marrow Transplantation Working Party Chronic Leukemia. 1995. Graft-versus-leukemia effect of Spender lymphocyte transfusions in marrow grafted patients. Blood 86: 2041-2050.
3. Kugler A., Stuhlet, G., Walden, P., Zoller, G., Zobywalski, A., Brossart, P., Trefzer, U., Ullrich, S., Muller, C. A., Becker, V., Gross, A. J., Hemmerlein, B., Kanz, L., Muller, G. A., and Ringert, R.-H. 2000. Regression of human metastatic renal cell carcinoma after vaccination with tumor cell-dendritic cell hybrids. Nature Med. 6: 332-336.
4. Kufe, D. 2000. Smallpox. polio and now a cancer vaccine? Nature Med. 6: 252-253.
5. Boczkowski, D., Nair, s. K., Nam, J. H., Lyerly, H. K. and Golboa, E. 2000. Induction of tumor immunity and cytotoxic T lymphocyte responses using dendritic cells transfected with messenger RNA amplified from tumor cells. Cancer Res. 60: 1028-1034.
6. Heiser, A., Dahm, P., Yancey, D., Maurice, M. A., Boczkowski, D., Nair, S. K., Gilboa, E. and Vieweg, J. 2000. Human dendritic cells transfected with RNA encoding prostate-specific antigen stimulate prostate-specific CTL responses in vitro. J. Immunol. 164: 5508-5014.
7. Nair, S. K., Boczkowski, D., Morse, M., Cumming, R. I., Lyerly, H. K. and Gilboa, E. 1998. Induction of primary carcinoembryonic antigen (CEA)-specific cytotoxic T lymphocytes in vitro using human dendritic cells transfected with RNA. Nat. Biotechnol 16: 364-369.
8. Nair, SK. Hull, S., Coleman, D., Gilboa, E., Lyerly, H. K. and Morse. M. A. 1999. Induction of carcinoembryonic antigen (CEA)-specific cytotoxic T-lymphocyte responses in vitro using autologous dendritic cells loaded with CEA peptide or CEA RNA in patients with metastatic malignancies expressing CEA. Int. J. Cancer 82: 121-124.
9. Dannull, J., Cemy, T., Ackermann, D. K. and Groettrup, M. 2000. Current status of dendritic cell-based tumor vaccination. Onkologie 23:544-551.
10, Visseren, M. J., van Elsas, A., van der Voort. E. I. H., Ressing, M. E., Ktist. W. M., Schrier, P. I. and C. J. M. Melief. 1995. CTL specific for the tyrosinase autoantigen can be induced from healthy Spender blood to lyse melanoma cells. J. Immunol. 154:3991-3998.
11. Su, Z., Peluso. M. V., Raffegerst, S. H., Schendel, D. J., and M. A. Roskrow. 2001. LMP2a-specific cytotoxic T lymphocytes for the treatment of patients with relapsed EBV-positive Hodgkin disease. Eur. J. Immunol. 31: 947-958.
12. Su, Z., Peluso, M. V., Raffergerst, S. U., Schendel, D. J., and Roskrow, M. Antigen presenting cells transfected with LMP2a RNA induce CD4+ LMP2a-specific cytotoxic T lymphocytes which kill via a Fas-independent mechanism (submitted).
13. Schendel, D. J., Gansbacher. B, Obemeder, R., Kriegmair, M., Hofstetter, A., Riethmüller, G., and O. G. Segurado. 1993. Tumor-specific lysis of human renal cell carcinomas by tumor-infiltrating lymphocytes. 1. HLA-A2 restricted lysis of autologous and aliogeneic tumor lines. J. Immunol, 151: 4209-4220.
14. Schendel, D. J., Frankenberger, B., Jantzer, P, Cayeux, S., Nöβner, E., Willimsky, G., Maget, B., Pohla, H.; and Th.

Blankenstein. 2000. Expression of B7.1 (CD80) in a renal cell carcinoma line allows expansion of tumor-associated cytotoxic T lymphocytes in the presence of an alloresponse. Gene Therapy 7: 2007-2014.
15. Jantzer, P. and D. J. Schendel. 1998. Human renal cell carcinoma antigen-specific cytotoxic T lymphocytes: antigen-driven selection and long-term persistence in vivo. Cancer Res. 58: 3078-3086.
16. Altman, J. D., Moss, P. A., Goulder, P. J., Barouch, D. H., McHeyzer-Willliams, M. G., Bell, J. 1., McMichael, A. J., and Davis, M. M. 1996. Phenotypic analysis of antigen-specific T Lymphocytes. Science 274: 94-96.
17. Gong, J., Nikrui, N., Chen, D., Koido, S., Wu, Z., Tanaka, Y., Cannistra, S., Avigan, D. and Kufe, D. 2000. Fusions of human ovarian carcinoma cells with autologous or allogeneic dendritic cells induce antitumor immunity. J. Immunol. 165: 1705-1711.

What is claimed is:

1. A method of treating a tumor disease in a patient, comprising administering to said patient a therapeutically effective amount of semi-allogeneic HLA-haploidentical antigen presenting cells into which proteins and/or peptides or RNA, DNA, or cDNA encoding said proteins and/or peptides have been introduced, wherein said semi-allogeneic HLA-haploidentical antigen-presenting cells have class I and class II molecules in common with the patient, wherein said proteins and/or peptides are selected from proteins providing a growth advantage to the tumor and/or ensuring its survival, cell cycle regulatory proteins, transcription factors, and proteins involved in the regulation of cell division.

2. The method of claim 1, wherein said proteins and/or peptides are selected from HER2/neu, PSMA, WT-1, mucins, or a telomerase.

3. The method of claim 2, wherein the mucin is MUC-1.

4. The method of claim 3, wherein said semi-allogeneic HLA-haploidentical antigen presenting cells are administered intravenously, subcutaneously, or intramuscularly.

5. The method of claim 1, wherein two different semi-allogeneic donors are used to provide the semi-allogeneic HLA-haploidentical antigen presenting cells.

6. The method of claim 1, wherein the semi-allogeneic HLA-haploidentical antigen presenting cells are monocytes, macrophages, or dendritic cells.

7. The method of claim 1, wherein the semi-allogeneic HLA-haploidentical antigen presenting cells have HLA-A, -B, or -C molecules in common with the patient.

8. The method of claim 1, wherein the semi-allogeneic HLA-haploidentical antigen presenting cells have HLA-DR, -DQ, or -DP molecules in common with the patient.

9. A method of treating a tumor disease in a patient, comprising administering to said patient a therapeutically effective amount of semi-allogeneic HLA-haploidentical antigen presenting cells into which proteins and/or peptides or RNA, DNA, or cDNA encoding said proteins and/or peptides have been introduced, wherein said semi-allogeneic HLA-haploidentical antigen-presenting cells have class I and class II molecules in common with the patient, wherein said proteins and/or peptides are selected from proteins providing a growth advantage to the tumor and/or ensuring its survival, cell cycle regulatory proteins, transcription factors, and proteins involved in the regulation of cell division, wherein said RNA has been reverse transcribed from tumor cells derived from the patient into cDNA, the cDNA has been amplified by means of PCR, and subsequently the cDNA has been transcribed into RNA.

* * * * *